United States Patent
Mohika

(10) Patent No.: US 9,499,318 B2
(45) Date of Patent: Nov. 22, 2016

(54) SYSTEM AND METHOD FOR CONTAINMENT AND ORGANIZATION OF MEDICAL WIRE

(71) Applicant: Cook Medical Technologies LLC, Bloomington, IN (US)

(72) Inventor: Brian O. Mohika, Lawrence, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 149 days.

(21) Appl. No.: 14/512,939

(22) Filed: Oct. 13, 2014

(65) Prior Publication Data

US 2016/0052689 A1 Feb. 25, 2016

Related U.S. Application Data

(60) Provisional application No. 62/040,305, filed on Aug. 21, 2014.

(51) Int. Cl.
*B65D 67/02* (2006.01)
*A61B 17/12* (2006.01)
(Continued)

(52) U.S. Cl.
CPC ........... *B65D 67/02* (2013.01); *A61B 17/1214* (2013.01); *A61B 17/28* (2013.01); *A61B 50/20* (2016.02); *A61M 25/002* (2013.01); *A61B 2017/2808* (2013.01); *A61M 2025/09125* (2013.01); *Y10T 24/44274* (2015.01);
(Continued)

(58) Field of Classification Search
CPC .................. Y10T 24/44274; Y10T 24/44538; Y10T 24/44906; Y10T 24/44615; Y10T 24/44654; Y10T 24/44752; Y10T 24/44769; Y10T 24/44915; A61M 5/1418
See application file for complete search history.

(56) References Cited

U.S. PATENT DOCUMENTS 3,503,397 A 3/1970 Fogarty et al.
3,503,398 A 3/1970 Fogarty et al.
(Continued)

FOREIGN PATENT DOCUMENTS

WO WO 00/06030 2/2000
WO WO 2004/066846 A1 8/2004
(Continued)

OTHER PUBLICATIONS

Medline Industries, Inc., "OR Necessities® Separate Sterile Pack Components" catalog, dated 2011, p. 25, Mundelein, IL.
(Continued)

*Primary Examiner* — Robert J Sandy
(74) *Attorney, Agent, or Firm* — Brinks Gilson & Lione

(57) ABSTRACT

A system for containment and organization of medical wire features a U-shaped clamp. A first ridged and grooved clamping block is located on a clamp first side posterior end and a second ridged and grooved clamping block is located on a clamp second side posterior end. A first side compression member is located on an inside surface of a clamp first side and a second side compression member is located on an inside surface of the clamp second side. An adjustable ratcheting lock attaches the clamp first side and the clamp second side. A first finger grip is located on an outside surface of the clamp first side and a second finger grip is located on an outside surface of the clamp second side. Medical wire is placed between the first side compression member and the second side compression member then the clamp is compressed against the medical wire.

16 Claims, 3 Drawing Sheets

(51) Int. Cl.
*A61B 17/28* (2006.01)
*A61M 25/00* (2006.01)
*A61M 25/09* (2006.01)

(52) U.S. Cl.
CPC ..... *Y10T 24/44538* (2015.01); *Y10T 24/44564* (2015.01); *Y10T 24/44615* (2015.01); *Y10T 24/44752* (2015.01); *Y10T 24/44906* (2015.01)

(56) References Cited

U.S. PATENT DOCUMENTS

| | | | | |
|---|---|---|---|---|
| 3,604,071 | A * | 9/1971 | Reimels | A61B 17/30 24/543 |
| 4,835,824 | A * | 6/1989 | Durham | A61B 17/12 24/339 |
| 5,022,126 | A * | 6/1991 | Davis | A61B 2017/280 24/346 |
| D333,182 | S | 2/1993 | Yoshikawa | |
| 5,226,892 | A * | 7/1993 | Boswell | A61M 5/1418 604/174 |
| 5,489,287 | A | 2/1996 | Green et al. | |
| 5,573,541 | A | 11/1996 | Green et al. | |
| 5,591,182 | A | 1/1997 | Johnson | |
| 5,944,729 | A | 8/1999 | Blake | |
| 6,099,539 | A | 8/2000 | Howell et al. | |
| 6,206,896 | B1 | 3/2001 | Howell et al. | |
| 6,228,104 | B1 | 5/2001 | Fogarty et al. | |
| 6,273,902 | B1 | 8/2001 | Fogarty et al. | |
| 6,293,954 | B1 | 9/2001 | Fogarty et al. | |
| 6,299,621 | B1 | 10/2001 | Fogarty et al. | |
| 6,387,106 | B1 | 5/2002 | Howell et al. | |
| 6,387,112 | B1 | 5/2002 | Fogarty et al. | |
| 6,406,485 | B1 | 6/2002 | Hossain et al. | |
| 6,460,231 | B2 * | 10/2002 | Bourgerie | A01K 97/08 24/487 |
| 6,530,942 | B2 | 3/2003 | Fogarty et al. | |
| 6,558,408 | B1 | 5/2003 | Fogarty et al. | |
| 6,579,304 | B1 | 6/2003 | Hart et al. | |
| 6,626,922 | B1 | 9/2003 | Hart et al. | |
| 6,692,514 | B2 | 2/2004 | Fogarty et al. | |
| 6,719,766 | B1 | 4/2004 | Buelna et al. | |
| 6,821,284 | B2 | 11/2004 | Sturtz et al. | |
| 6,942,676 | B2 | 9/2005 | Buelna | |
| 6,989,017 | B2 | 1/2006 | Howell et al. | |
| 7,322,995 | B2 | 1/2008 | Buckman et al. | |
| 7,578,827 | B2 | 8/2009 | Gadberry et al. | |
| 7,780,688 | B2 | 8/2010 | Sakakine et al. | |
| 7,850,702 | B2 | 12/2010 | Sorribes | |
| 8,092,473 | B2 | 1/2012 | Hart et al. | |
| 8,167,252 | B2 * | 5/2012 | Nitsche | A61B 5/04085 24/562 |
| 8,201,310 | B1 | 6/2012 | Abdi et al. | |
| 8,273,102 | B2 | 9/2012 | Danitz et al. | |
| 8,578,571 | B2 | 11/2013 | Schmidt et al. | |
| 2011/0210215 | A1 * | 9/2011 | Nitsche | A61B 5/04085 248/74.1 |
| 2011/0313437 | A1 | 12/2011 | Yeh | |
| 2013/0212844 | A1 | 8/2013 | Chen | |

FOREIGN PATENT DOCUMENTS

WO WO 2005/048854 A2 6/2005
WO WO 2005/096960 A1 10/2005

OTHER PUBLICATIONS

Cook Medical Technologies LLC, "Clip", at least as early as Aug. 20, 2014, 2 pgs.
Extended European Search Report, dated Jan. 20, 2016, pp. 1-12, issued in European Patent Application No. 15180264.2-1654, European Patent Office, Munich, Germany.

* cited by examiner

SYSTEM AND METHOD FOR CONTAINMENT AND ORGANIZATION OF MEDICAL WIRE

CROSS REFERENCE

This application claims priority to U.S. Provisional Patent Application No. 62/040,305 filed Aug. 21, 2014, the specification(s) of which is/are incorporated herein in their entirety by reference.

FIELD OF THE INVENTION

The present invention relates to medical devices, systems, and methods, and more specifically, medical wire devices, medical wire systems, and methods of containing and organizing medical wire.

BACKGROUND OF THE INVENTION

Wire used for medical purposes is carefully manufactured, sterilized, and sealed in a sterilized package in preparation for use. Once removed from the package, this wire can be difficult to handle and keep separate from other medical wires of a different size, especially in a pressure-filled environment. It can even be slippery at times. The present invention features a system and method for containment and organization of medical wire.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a system for containment and organization of medical wire. In some embodiments, the system comprises a clamp. In some embodiments, the clamp comprises a shape of a "U". In some embodiments, a first ridged and grooved clamping block is angularly located on a clamp first side posterior end and a second ridged and grooved clamping block is angularly located on a clamp second side posterior end. In some embodiments, the first ridged and grooved clamping block interfaces with the second ridged and grooved clamping block upon closure of the clamp.

In some embodiments, the system comprises a first side compression member. In some embodiments, the first side compression member is located on an inside surface of a clamp first side next to the first ridged and groove clamping block and projects out and away from the clamp first side toward a clamp second side. In some embodiments, the first side compression member comprises a shape of a rectangular prism. In some embodiments, the first side compression member is elastomeric.

In some embodiments, the system comprises a second side compression member. In some embodiments, the second side compression member is located on an inside surface of the clamp second side next to the second ridged and groove clamping block and projects out and away from the clamp second side toward the clamp first side. In some embodiments, the second side compression member comprises a shape of a rectangular prism. In some embodiments, the second side compression member is elastomeric.

In some embodiments, the system comprises an adjustable ratcheting lock located between and attaching the clamp first side and the clamp second side. In some embodiments, a ratcheting lock first end is located on the inside surface of the clamp first side between the clamp first side posterior end and a clamp anterior end and a ratcheting lock second end is located on the inside surface of the clamp second side between the clamp second side posterior end and the clamp anterior end.

In some embodiments, the system comprises a first finger grip located on an outside surface of the clamp first side opposed to the ratcheting lock first end and a second finger grip located on an outside surface of the clamp second side opposed to the ratcheting lock second end.

In some embodiments, medical wire is placed in an open clamp between the first side compression member and the second side compression member. In some embodiments, the clamp is closed having the first ridged and grooved clamping block interlocked against the second ridged and grooved clamping block. In some embodiments, the adjustable ratcheting lock is tightened via manually pinching the clamp via the first finger grip and the second finger grip to compress the first side compression member and the second side compression member against the medical wire for securely holding into position.

DESCRIPTION OF PREFERRED EMBODIMENTS

Figure 1:
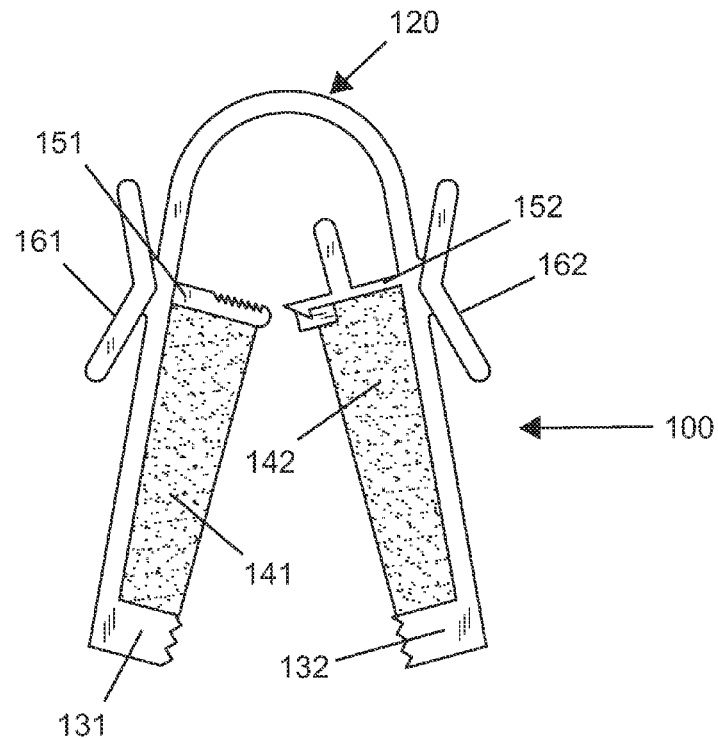
FIG. 1 shows a front view of the present invention, unclamped.
Figure 2:
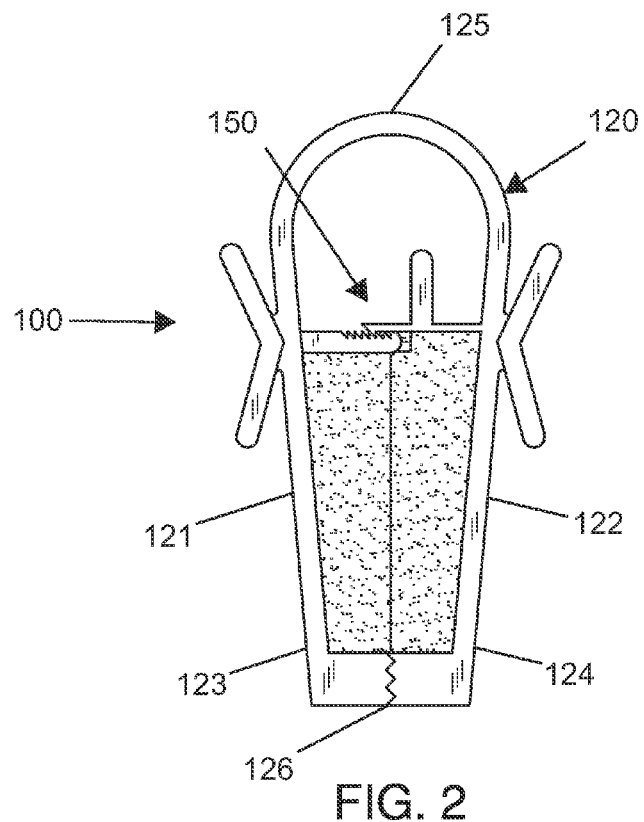
FIG. 2 shows a front view of the present invention, clamped.
Figure 3:
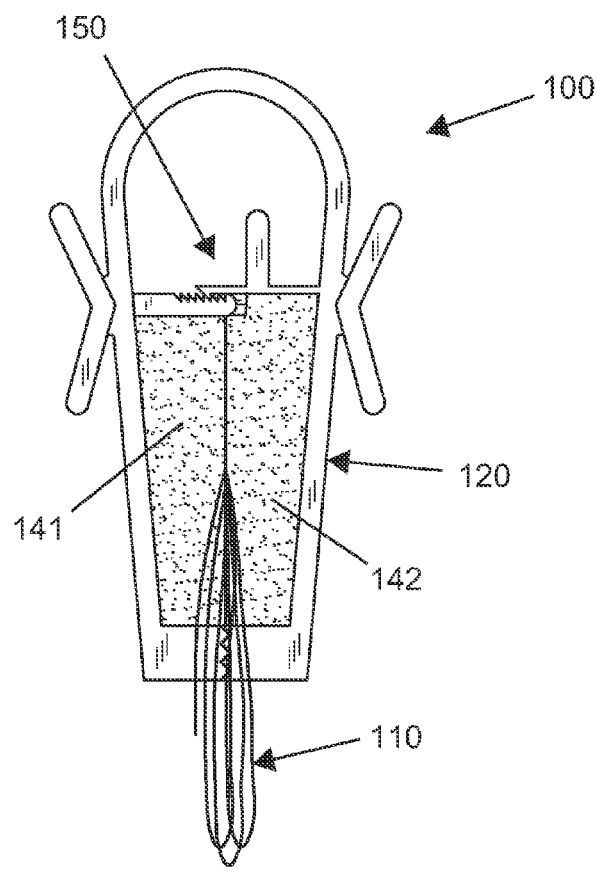
FIG. 3 shows a front view of the present invention, clamped on medical wire.
Figure 4:
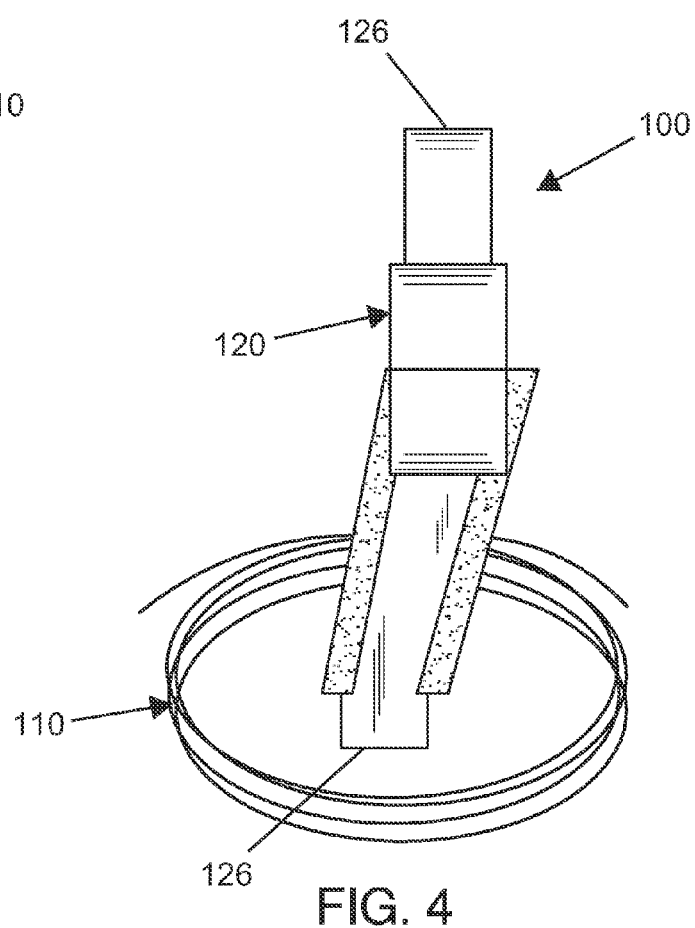
FIG. 4 shows a side view of the present invention, clamped on medical wire.
Figure 5:
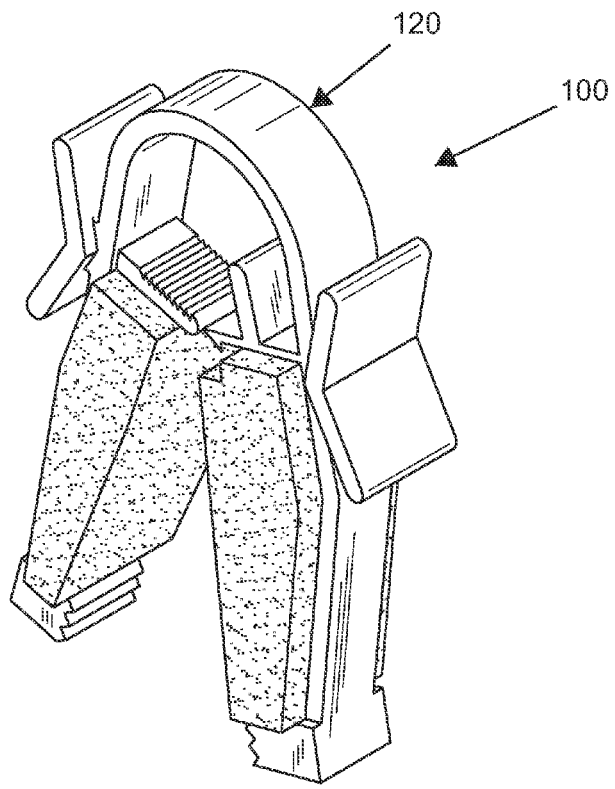
FIG. 5 shows a perspective view of the present invention, unclamped.
Figure 6:
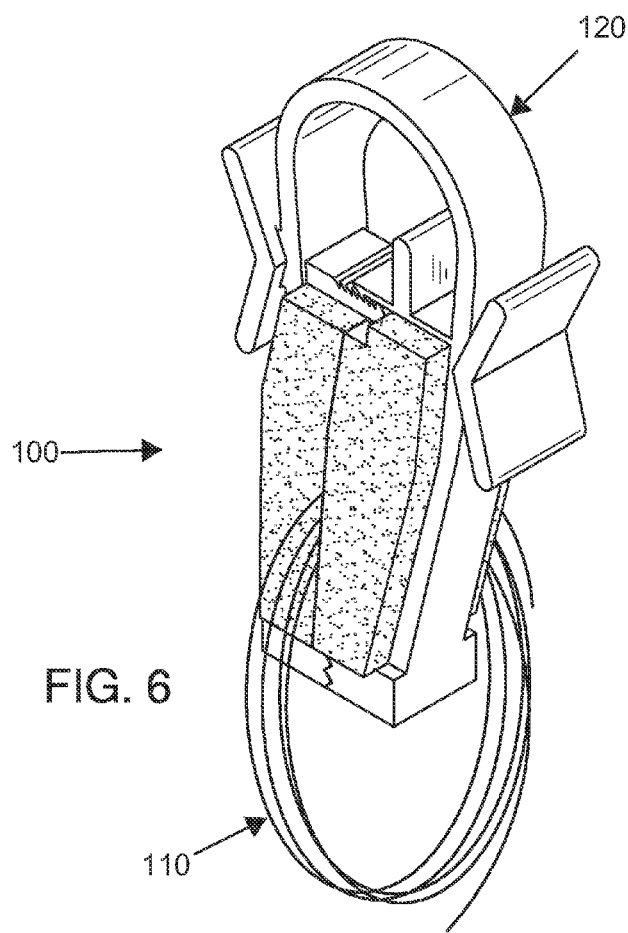
FIG. 6 shows a perspective view of the present invention, clamped on medical wire.

Following is a list of elements corresponding to a particular element referred to herein:

100 Medical wire containment and organization system
110 Medical wire
120 Clamp
121 Clamp first side
122 Clamp second side
123 Clamp first side posterior end
124 Clamp second side posterior end
125 Clamp anterior end
126 Clamp posterior end
131 First ridged and grooved clamping block
132 Second ridged and grooved clamping block
141 First side compression member
142 Second side compression member
150 Ratcheting lock
151 Ratcheting lock first end
152 Ratcheting lock second end
161 First finger grip
162 Second finger grip Referring now to FIG. 1-6, the present invention features a system (100) for containment and organization of medical wire. In some embodiments, the system (100) comprises a clamp (120) having a clamp first side (121), a clamp second side (122), a clamp anterior end (125), and a clamp posterior end (126). In some embodiments, the clamp (120) comprises a shape of a "U". In some embodiments, the clamp (120) comprises a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) is angularly located on the clamp first side posterior end (123) and a second ridged and grooved clamping block (132) is angularly located on the clamp second side posterior end (124). In some embodiments, the first ridged and grooved clamping block (131) mates and interfaces with the second ridged and grooved clamping block (132) upon closure of the clamp (120). In some embodiments, the first ridged and grooved clamping block (131) and the second ridged and grooved clamping block (132) are positioned at a 90 degree angle with respect to the clamp first side (121) and the clamp second side (122), respectively. In some embodiments, the first ridged and grooved clamping block (131) and the second ridged and grooved clamping block (132) are positioned at a 75 degree angle with respect to the clamp first side (121) and the clamp second side (122), respectively. In some embodiments, the first ridged and grooved clamping block (131) and the second ridged and grooved clamping block (132) are positioned at a 60 degree angle with respect to the clamp first side (121) and the clamp second side (122), respectively. In some embodiments, the first ridged and grooved clamping block (131) and the second ridged and grooved clamping block (132) are positioned at a 45 degree angle with respect to the clamp first side (121) and the clamp second side (122), respectively. In some embodiments, the first ridged and grooved clamping block (131) and the second ridged and grooved clamping block (132) are positioned at a 105 degree angle with respect to the clamp first side (121) and the clamp second side (122), respectively. In some embodiments, the first ridged and grooved clamping block (131) and the second ridged and grooved clamping block (132) are positioned at a 120 degree angle with respect to the clamp first side (121) and the clamp second side (122), respectively. In some embodiments, the first ridged and grooved clamping block (131) and the second ridged and grooved clamping block (132) are positioned at a 135 degree angle with respect to the clamp first side (121) and the clamp second side (122), respectively.

In some embodiments, the system (100) comprises a first side compression member (141). In some embodiments, the first side compression member (141) is located on an inside surface of the clamp first side (121) next to the first ridged and grooved clamping block (131) and projects out and away from the clamp first side (121) toward the clamp second side (122). In some embodiments, the first side compression member (141) comprises a shape of a rectangular prism. In some embodiments, the first side compression member (141) is elastomeric.

In some embodiments the first side compression member (141) is constructed of foam. In some embodiments the first side compression member (141) is constructed of rubber. In some embodiments the first side compression member (141) is constructed of latex. In some embodiments the first side compression member (141) comprises a planar interfacing surface.

In some embodiments, the system (100) comprises a second side compression member (142). In some embodiments, the second side compression member (142) is located on an inside surface of the clamp second side (122) next to the second ridged and grooved clamping block (132) and projects out and away from the clamp second side (122) toward the clamp first side (121). In some embodiments, the second side compression member (142) comprises a shape of a rectangular prism. In some embodiments, the second side compression member (142) is elastomeric.

In some embodiments the second side compression member (142) is constructed of foam. In some embodiments the second side compression member (142) is constructed of rubber. In some embodiments the second side compression member (142) is constructed of latex. In some embodiments the second side compression member (142) comprises a planar interfacing surface.

In some embodiments, the system (100) comprises an adjustable ratcheting lock (150) located between and attaching the clamp first side (121) and the clamp second side (122) in a releasable manner. In some embodiments, a ratcheting lock first end (151) is located on the inside surface of the clamp first side (121) between the clamp first side posterior end (123) and the clamp anterior end (125) and a ratcheting lock second end (152) is located on the inside surface of the clamp second side (122) between the clamp second side posterior end (124) and the clamp anterior end (125). In some embodiments, the adjustable ratcheting lock (150) comprises a plurality of settings corresponding to a level of compression between the first side compression member (141) and the second side compression member (142).

In some embodiments, the system (100) comprises a first finger grip (161) located on an outside surface of the clamp first side (121) opposed to the ratcheting lock first end (151) and a second finger grip (162) located on an outside surface of the clamp second side (122) opposed to the ratcheting lock second end (152).

In some embodiments, medical wire (110) is placed in an open clamp (120) between the first side compression member (141) and the second side compression member (142). In some embodiments, the clamp (120) is closed having the first ridged and grooved clamping block (131) interfacing and interlocked against the second ridged and grooved clamping block (132). In some embodiments, the adjustable ratcheting lock (150) is tightened via manually pinching the clamp (120) via the first finger grip (161) and the second finger grip (162) to compress the first side compression member (141) and the second side compression member (142) against the medical wire (110) for securely holding into position.

In some embodiments, the first side compression member (141) is located on the inside surface of the clamp first side (121) and the second side compression member (142) is located on the inside surface of the clamp second side (122) via a water resistant adhesive.

In some embodiments, the first side compression member (141) is located on the inside surface of the clamp first side (121) and the second side compression member (142) is located on the inside surface of the clamp second side (122) via a saline compatible adhesive.

In some embodiments, the first side compression member (141) is located on the inside surface of the clamp first side (121) and the second side compression member (142) is located on the inside surface of the clamp second side (122) via mechanical fastening.

In some embodiments, the system (100) further comprises medical wire (110).

In some embodiments, the medical wire (110) is interventional procedure wire.

In some embodiments, the medical wire (110) is cardiac catheterizing wire.

In some embodiments, the medical wire (110) is hydrophilic wire.

In some embodiments, the medical wire (110) is micro wire.

In some embodiments, the medical wire (110) is guide wire.

In some embodiments, the medical wire (110) is a catheter.

In some embodiments, the system (100) further comprises a catheter and guide wire bowl. In some embodiments, the system (100) further comprises a bowl.

In some embodiments, the system (100) further comprises a plurality of clamps (120). In some embodiments, the system (100) further comprises a plurality of color coded clamps (120). In some embodiments, the system (100) further comprises a plurality of labeled clamps (120).

In some embodiments, the system (100) further comprises an indicator located on each clamp (120) for indicating wire type or size.

In some embodiments, the indicator is a unique color.

A method of containment and organization of medical wire comprises obtaining a system (100) for containment and organization of medical wire comprising a clamp (120) having a clamp first side (121), a clamp second side (122), a clamp anterior end (125), and a clamp posterior end (126). In some embodiments, the clamp (120) comprises a shape of a "U". In some embodiments, the clamp (120) comprises a terminating clamp first side posterior end (123) located on the clamp first side (121) at the clamp posterior end (126), a terminating clamp second side posterior end (124) located on the clamp second side (122) at the clamp posterior end (126), with the arcuate clamp anterior end (125) joining the clamp first side (121) to the clamp second side (122). In some embodiments, a first ridged and grooved clamping block (131) is angularly located on the clamp first side posterior end (123) and a second ridged and grooved clamping block (132) is angularly located on the clamp second side posterior end (124). In some embodiments, the first ridged and grooved clamping block (131) mates with and interlaces with the second ridged and grooved clamping block (132) upon closure of the clamp (120). In some embodiments, the system (100) comprises a first side compression member (141). In some embodiments, the first side compression member (141) is located on an inside surface of the clamp first side (121) next to the first ridged and grooved clamping block (131) and projects out and away from the clamp first side (121) toward the clamp second side (122). In some embodiments, the first side compression member (141) comprises a shape of a rectangular prism. In some embodiments, the first side compression member (141) is elastomeric. In some embodiments, the system (100) comprises a second side compression member (142). In some embodiments, the second side compression member (142) is located on an inside surface of the clamp second side (122) next to the second ridged and grooved clamping block (132) and projects out and away from the clamp second side (122) toward the clamp first side (121). In some embodiments, the second side compression member (142) comprises a shape of a rectangular prism. In some embodiments, the second side compression member (142) is elastomeric. In some embodiments, the system (100) comprises an adjustable ratcheting lock (150) located between and releasably attaching the clamp first side (121) and the clamp second side (122). In some embodiments, a ratcheting lock first end (151) is located on the inside surface of the clamp first side (121) between the clamp first side posterior end (123) and the clamp anterior end (125) and a ratcheting lock second end (152) is located on the inside surface of the clamp second side (122) between the clamp second side posterior end (124) and the clamp anterior end (125). In some embodiments, the system (100) comprises a first finger grip (161) located on an outside surface of the clamp first side (121) opposed to the ratcheting lock first end (151) and a second finger grip (162) located on an outside surface of the clamp second side (122) opposed to the ratcheting lock second end (152). In some embodiments, the system (100) comprises medical wire (110). In some embodiments, the system (100) comprises a catheter and guide wire bowl.

In some embodiments, the method comprises removing the medical wire (110) from its sterile packaging.

In some embodiments, the method comprises placing medical wire (110) in an open clamp (120) between the first side compression member (141) and the second side compression member (142) in either a straight or a looped position having at least one strand of the medical wire (110) in contact with the first side compression member (141) and the second side compression member (142).

In some embodiments, the method comprises closing the clamp (120) with the first ridged and grooved clamping block (131) interfacingly interlocked against the second ridged and grooved clamping block (132).

In some embodiments, the method comprises tightening the clamp (120) with the adjustable ratcheting lock (150) via manually pinching the clamp (120) via the first finger grip (161) and the second finger grip (162) to compress the first side compression member (141) and the second side compression member (142) against the medical wire (110) for securely holding into position.

In some embodiments, the method comprises placing the clamp (120) with the medical wire (110) into the catheter and guide wire bowl in preparation for use.

In some embodiments, the method comprises discarding the clamp (120) after a single use.

In some embodiments, the method comprises a plurality of clamps (120) used with a plurality of medical wires (110). In some embodiments, the plurality of clamps (120) comprise a unique indicator located on each clamp (120) for indicating wire type or size.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system (100) for containment and organization of medical wire, wherein the system (100) comprises:
   (a) a clamp (120) having a clamp first side (121), a clamp second side (122), an arcuate clamp anterior end (125), and a clamp posterior end (126), wherein the clamp (120) comprises a shape of a "U", wherein the clamp (120) comprises a terminating clamp first side posterior end (123) disposed on the clamp first side (121) at the clamp posterior end (126), a terminating clamp second side posterior end (124) disposed on the clamp second side (122) at the clamp posterior end (126), with the arcuate clamp anterior end (125) joining the clamp first side (121) to the clamp second side (122), wherein a first ridged and grooved clamping block (131) is angularly disposed on the clamp first side posterior end (123) and a second ridged and grooved clamping block (132) is angularly disposed on the clamp second side posterior end (124), wherein the first ridged and grooved clamping block (131) matably interfaces with the second ridged and grooved clamping block (132) upon closure of the clamp (120);
   (b) a first side compression member (141), wherein the first side compression member (141) is disposed on an inside surface of the clamp first side (121) adjacent to the first ridged and grooved clamping block (131) and projects out and away from the clamp first side (121) toward the clamp second side (122), wherein the first side compression member (141) comprises a shape of a rectangular prism, wherein the first side compression member (141) is elastomeric;
   (c) a second side compression member (142), wherein the second side compression member (142) is disposed on an inside surface of the clamp second side (122) adjacent to the second ridged and grooved clamping block (132) and projects out and away from the clamp second side (122) toward the clamp first side (121), wherein the second side compression member (142) comprises a shape of a rectangular prism, wherein the second side compression member (142) is elastomeric;
   (d) an adjustable ratcheting lock (150) disposed between and releasably attaching the clamp first side (121) and the clamp second side (122), wherein a ratcheting lock first end (151) is disposed on the inside surface of the clamp first side (121) between the clamp first side posterior end (123) and the arcuate clamp anterior end (125) and a ratcheting lock second end (152) is disposed on the inside surface of the clamp second side (122) between the clamp second side posterior end (124) and the arcuate clamp anterior end (125); and
   (e) a first finger grip (161) disposed on an outside surface of the clamp first side (121) opposed to the ratcheting lock first end (151) and a second finger grip (162) disposed on an outside surface of the clamp second side (122) opposed to the ratcheting lock second end (152); wherein medical wire (110) is placed in an open clamp (120) between the first side compression member (141) and the second side compression member (142), wherein the clamp (120) is closed having the first ridged and grooved clamping block (131) interfacingly interlocked against the second ridged and grooved clamping block (132), wherein the adjustable ratcheting lock (150) is tightened via manually pinching the clamp (120) via the first finger grip (161) and the second finger grip (162) to compress the first side compression member (141) and the second side compression member (142) against the medical wire (110) for securely holding into position.

2. The system (100) of claim 1, wherein the first side compression member (141) is disposed on the inside surface of the clamp first side (121) and the second side compression member (142) is disposed on the inside surface of the clamp second side (122) via a water resistant adhesive.

3. The system (100) of claim 1, wherein the first side compression member (141) is disposed on the inside surface of the clamp first side (121) and the second side compression member (142) is disposed on the inside surface of the clamp second side (122) via a saline compatible adhesive.

4. The system (100) of claim 1, further comprising medical wire (110).

5. The system (100) of claim 4, wherein the medical wire (110) is interventional procedure wire.

6. The system (100) of claim 4, wherein the medical wire (110) is cardiac catheterizing wire.

7. The system (100) of claim 4, wherein the medical wire (110) is hydrophilic wire.

8. The system (100) of claim 4, wherein the medical wire (110) is micro wire.

9. The system (100) of claim 4, wherein the medical wire (110) is guide wire.

10. The system (100) of claim 4, wherein the medical wire (110) is a catheter.

11. The system (100) of claim 1 further comprising a catheter and guide wire bowl.

12. The system (100) of claim 1, comprising a plurality of clamps (120).

13. The system (100) of claim 12, comprising an indicator disposed on each clamp (120) for indicating wire type or size.

14. The system (100) of claim 13, wherein the indicator is a unique color.

15. A method of containment and organization of medical wire, wherein the method comprises:
   (a) obtaining a system (100) for containment and organization of medical wire comprising a clamp (120) having a clamp first side (121), a clamp second side (122), an arcuate clamp anterior end (125), and a clamp posterior end (126), wherein the clamp (120) comprises a shape of a "U", wherein the clamp (120) comprises a terminating clamp first side posterior end (123) disposed on the clamp first side (121) at the clamp posterior end (126), a terminating clamp second side posterior end (124) disposed on the clamp second side (122) at the clamp posterior end (126), with the arcuate clamp anterior end (125) joining the clamp first side (121) to the clamp second side (122), wherein a first ridged and grooved clamping block (131) is angularly disposed on the clamp first side posterior end (123) and a second ridged and grooved clamping block (132) is angularly disposed on the clamp second side posterior end (124), wherein the first ridged and grooved clamping block (131) matably interfaces with the second ridged and grooved clamping block (132) upon closure of the clamp (120); a first side compression member (141), wherein the first side compression member (141) is disposed on an inside surface of the clamp first side (121) adjacent to the first ridged and grooved clamping block (131) and projects out and away from the clamp first side (121) toward the clamp second side (122), wherein the first side compression member (141) comprises a shape of a rectangular prism, wherein the first side compression member (141) is elastomeric; a second side compression member (142), wherein the second side compression member (142) is disposed on an inside surface of the clamp second side (122) adjacent to the second ridged and grooved clamping block (132) and projects out and away from the clamp second side (122) toward the clamp first side (121), wherein the second side compression member (142) comprises a shape of a rectangular prism, wherein the second side compression member (142) is elastomeric; an adjustable ratcheting lock (150) disposed between and releasably attaching the clamp first side (121) and the clamp second side (122), wherein a ratcheting lock first end (151) is disposed on the inside surface of the clamp first side (121) between the clamp first side posterior end (123) and the arcuate clamp anterior end (125) and a ratcheting lock second end (152) is disposed on the inside surface of the clamp second side (122) between the clamp second side posterior end (124) and the arcuate clamp anterior end (125); a first finger grip (161) disposed on an outside surface of the clamp first side (121) opposed to the ratcheting lock first end (151) and a second finger grip (162) disposed on an outside surface of the clamp second side (122) opposed to the ratcheting lock second end (152); medical wire (110); and a catheter and guide wire bowl;

(b) removing the medical wire (110) from its sterile packaging;

(c) placing medical wire (110) in an open clamp (120) between the first side compression member (141) and the second side compression member (142) in either a straight or a looped position having at least one strand of the medical wire (110) in contact with the first side compression member (141) and the second side compression member (142);

(d) closing the clamp (120) with the first ridged and grooved clamping block (131) interfacingly interlocked against the second ridged and grooved clamping block (132);

(e) tightening the clamp (120) with the adjustable ratcheting lock (150) via manually pinching the clamp (120) via the first finger grip (161) and the second finger grip (162) to compress the first side compression member (141) and the second side compression member (142) against the medical wire (110) for securely holding into position; and (f) placing the clamp (120) with the medical wire (110) into the catheter and guide wire bowl in preparation for use.

16. The method of claim 15, further comprising a plurality of clamps (120) used with a plurality of medical wires (110), wherein the plurality of clamps (120) comprise a unique indicator disposed on each clamp (120) for indicating wire type or size.

* * * * *